United States Patent [19]

Sakai et al.

[11] Patent Number: 4,937,038

[45] Date of Patent: Jun. 26, 1990

[54] SOLUTION QUANTITATIVE ANALYSIS APPARATUS, QUANTITATIVE ANALYSIS METHODS, AND NUCLEAR REACTOR WATER QUALITY CONTROL SYSTEM

[75] Inventors: Masanori Sakai; Katsumi Ohsumi, both of Hitachi; Noriyuki Ohnaka; Eiji Kikuchi, both of Katsuta; Katsumi Mabuchi; Takuya Takahashi, both of Hitachi, all of Japan

[73] Assignee: Hitachi, Ltd., Tokyo, Japan

[21] Appl. No.: 281,212

[22] Filed: Dec. 8, 1988

[30] Foreign Application Priority Data

Dec. 11, 1987 [JP] Japan .................. 62-311969
May 17, 1988 [JP] Japan .................. 63-119125

[51] Int. Cl.$^5$ ................ G21C 17/02; G01N 27/26
[52] U.S. Cl. ......................... 376/245; 376/256; 422/80; 436/135; 204/153.1; 204/153.11; 204/153.18; 204/153.21; 204/412
[58] Field of Search ............ 376/245, 256; 204/1 T, 204/1 Y, 400, 412, 413, 434; 436/135, 153; 422/80; 73/26, 27 R, 61.1 R, 61.1 C, 863

[56] References Cited

U.S. PATENT DOCUMENTS

| | | |
|---|---|---|
| 4,225,410 | 9/1980 | Pace .................. 204/412 |
| 4,520,654 | 6/1985 | Terhune .................. 376/256 |
| 4,571,292 | 2/1986 | Liu et al. .................. 204/412 |
| 4,605,900 | 8/1986 | Moilanen et al. .................. 204/412 |
| 4,636,292 | 1/1987 | Fejes et al. .................. 376/245 |
| 4,707,242 | 11/1987 | Schneider et al. .................. 204/412 |
| 4,759,902 | 7/1988 | Anstine .................. 376/245 |
| 4,822,474 | 4/1989 | Corrado .................. 204/412 |

FOREIGN PATENT DOCUMENTS

| | | |
|---|---|---|
| 143437 | 11/1980 | Japan . |
| 146035 | 11/1980 | Japan . |
| 238791 | 11/1985 | Japan . |
| 148394 | 7/1986 | Japan . |
| 164194 | 7/1986 | Japan . |

Primary Examiner—Daniel Wasil
Attorney, Agent, or Firm—Antonelli, Terry, Stout & Kraus

[57] ABSTRACT

This invention comprises electrochemical analytical devices capable of performing electrolysis in multiple pulse modes. It relates to a method of quantitative analysis and equipment for performing quantitative analysis which uses a combinaiton of these pulse modes to realize the measurement of concentrations of multiple substances to be measured, occurring in the test solution to be measured and also a nuclear reactor water quality control system employing such a quantitative analysis method.

25 Claims, 14 Drawing Sheets (SQUARE-WAVE PULSE VOLTAMMETRY)

(DIFFERENTIAL NORMAL PULSE VOLTAMMETRY)

(REVERSE PULSE VOLTAMMETRY)

(DIFFERENTIAL NORMAL PULSE VOLTAMMETRY)

SOLUTION QUANTITATIVE ANALYSIS APPARATUS, QUANTITATIVE ANALYSIS METHODS, AND NUCLEAR REACTOR WATER QUALITY CONTROL SYSTEM

BACKGROUND OF THE INVENTION

1. Field of the Invention

This invention relates to quantitative analysis methods and a quantitative analysis apparatus for measuring plural kinds of substances to be analyzed occurring in a sample solution, and relates to a water quality control system based on such quantitative methods, intended for water quality control for nuclear reactors.

This invention is suitably applicable to water quality testing and control in boiling water reactors (BWR) and pressurized water reactors (PWR).

2. Description of the Prior Art

The water used in nuclear reactors contains dissolved gases of $H_2$, $O_2$, and $H_2O_2$. The amounts of these dissolved gases change as the gases circulate in the nuclear reactor cooling system. For each gas, there is a maximum tolerable limit, beyond which the gas can corrode the reactor pipes, posing a potential danger of water leak or even pipe breakage.

Therefore, an important requirement is to sample the high-temperature, high-pressure water circulating in the cooling system of a nuclear reactor, perform quantitative analyses of $H_2$, $O_2$, and $H_2O_2$, and ensure adequate control of the water quality based on the results of analyses.

Among the means of simultaneously detecting dissolved $O_2$ and $H_2O_2$ contained in the reactor water in a nuclear reactor is a method of simultaneously measuring dissolved oxygen and hydrogen peroxide by using a dissolved oxygen meter and a hydrogen peroxide decomposition activated charcoal column, published in Japanese Patent Kokai (Laid open) No. 55-142437.

The above prior art, however, provides no specific information on performing quantitative analysis of dissolved oxygen in the reactor water. It is unclear whether or not the said prior art is applicable to the analysis of high-temperature, high-pressure water that is found in the primary cooling system of a nuclear reactor.

SUMMARY OF THE INVENTION

The purpose of the present invention is to provide quantitative analysis apparatus capable of simultaneous in situ analysis of $H_2$, $O_2$, and $H_2O_2$, which are contained in the reactor water of a nuclear reactor.

Another purpose of this invention is to provide a quantitative analysis method allowing simultaneous quantitative analysis of $H_2$, $O_2$, and $H_2O_2$ in a solution by electrolysis.

Yet another purpose of this invention is to provide a nuclear reactor water quality control system based on in situ quantitative analysis of $H_2$, $O_2$, and $H_2O_2$ contained in the reactor water of a nuclear reactor.

Still another purpose of this invention is to provide a preventive safety assurance system allowing in situ quantitative analysis of $H_2$, $O_2$, and $H_2O_2$, contained in the reactor water of a nuclear reactor, by comparing the analytical results with standard values, to detect danger signals in the cooing system, such as potential reactor water leaks.

The quantitative analysis apparatus of this invention comprises an electrolytic cell containing a working electrode, a counter electrode, and a reference electrode for electrolyzing (3 electrodes or 2 electrodes systems) the sample solution; a means of applying voltage-time waveform signals, having different parameters for each chemical species to be analyzed and present in the sample solution, to the working electrode in the electrolytic cell, as standard voltage from the reference electrode; a means of determining limiting current or peak current values, based on the electrolysis current which is obtained by electrolyzing the sample solution by applying the said waveform signals, and based on the voltage required to produce the electrolysis current; and a means of calculating the concentrations of the target chemical species, based on the limiting current or peak current thus obtained.

The voltage-time waveform signal applied to the working electrode in the electrolytic cell has certain parameters which are determined by the kind of voltammetry employed.

When a solution containing $H_2$ and $H_2O_2$ or a solution containing $O_2$ and $H_2O_2$ is electrolyzed by simple electrochemical procedures, the observed electrolysis current contains current components for both $H_2$ and $H_2O_2$ or both $O_2$ and $H_2O_2$, and it is impossible to determine the individual concentrations of $H_2$, $O_2$, and $H_2O_2$.

The present invention is based on a novel idea: On a solution containing two chemical species, $H_2O_2$ and either $H_2$ or $O_2$, two kinds of voltammetry are performed; similarly, on a solution containing three chemical species, $H_2$, $O_2$, and $H_2O_2$, three kinds of voltammetry are performed. Each voltammetry is performed by changing the parameters for the voltage-time waveform signals which are applied to the electrolytic cell, thus allowing simultaneous determination of the individual concentrations of $H_2$, $O_2$, and $H_2O_2$.

Electrolytic analysis is well suited to in situ quantitative analysis of high-temperature, high-pressure water in the primary cooling system of a nuclear reactor. Further, its fast concentration determination capability lends itself to rapid control of water quality for the reactor water.

A favored method of voltammetry for the purpose of this invention is the pulse-mode pulse voltammetry. In the embodiments of this invention, to be described later, we obtained favorable results by using normal pulse voltammetry and differential pulse voltammetry.

The types of pulse voltammetry that can be used for the purpose of this invention include: normal pulse voltammetry, reverse pulse voltammetry, differential voltammetry, differential normal pulse voltammetry, and square-wave pulse voltammetry.

A discussion of the pulse mode in a computerized pulse voltammetry may be found in Analytical Chemistry, Vol. 43, No. 3, March 1971, pp. 342-348.

Detailed description of differential normal pulse voltammetry may be found in the Journal of Electroanalytical Chemistry, 110 (1980) pp. 1-18.

Application of square-wave voltammetry to quantitative analysis is discussed in Analytical Chemistry, 49, 13 (1977) pp. 1904-1908 and in Analytical Chemistry 36 (1987) pp. 420-424.

Discussions on normal pulse voltammetry, differential pulse voltammetry, and reverse pulse voltammetry, and a comprehensive theory on pulse voltammetry, may be found in the Bulletin of Chemical Society of Japan 53 (1980) pp. 3439-3446, and the Journal of Electroanalytical Chemistry 205 (1986) pp. 21-34.

However, in the above publications pulse voltammetry is discussed from a purely electrochemical standpoint. Until now, most of the discussions concerning the applicability of pulse voltammetry to quantitative analysis have centered on the merits of analytical methods using a single pulse mode, the reason being that pulse voltammetry employed in single mode offers the highest precision among the current voltammetry methods, and that for most quantitative analysis purposes the attainable precision of the single pulse mode is sufficient. However, there has been little discussion on quantitative analytical methods employing a combination of several types of pulse modes.

In the quantitative analysis apparatus for the purpose of this invention, a potentiostat should be provided as a means of applying voltage-time waveform signals to the working electrode in the electrolytic cell, and a CPU should be provided for supplying the waveform signals to the potentiostat.

The CPU should provide the following features: a signal input unit for entering into the potentiostat voltage-time waveform signals having specified parameters according to the kind of voltammetry employed; a storage unit for storing in memory the results of voltammetry analyses, for each chemical species in the sample solution to be analyzed and treated by the potentiostat, as a relationship between the electrolysis current and the voltage required to produce the electrolysis current; a current determination unit which processes the data stored in the storage unit and which determines the limiting current or peak current values according to the kind of voltammetry employed; and a computation unit which calculates the concentrations of the desired chemical species, based on the determined limiting current or the peak current values.

The function of the potentiostat is to accurately apply the voltage-time waveform signals, supplied by the CPU with function generators, as reference electrode standard voltage to the working electrode.

The quantitative analysis method of this invention comprises the following processes: a process of contacting the three electrodes in an electrolytic cell of a working electrode, a counter electrode, and a reference electrode with the solution containing the multiple chemical species to be analyzed; a process of electrolyzing said solution, by applying to the electrolytic cell different voltage-time waveform signals for each chemical species to be analyzed; a process of determining limiting current or peak current values according to the kind of voltammetry employed, based on the electrolysis current obtained during the electrolysis process and the voltage required to produce the electrolysis current; and a process of calculating the concentrations of the desired multiple chemical species, based on the limiting current or peak current values thus obtained.

In the above computation process, an equation in which the concentrations of the desired substances are treated as unknown variables is set up for each voltammetry, and the concentrations of the desired substances are determined by solving these equations as a set of simultaneous equations.

The water quality control system of this invention provides a means of performing quantitative analysis, based on electrolysis, on the reactor water from the primary cooling system of a nuclear reactor; and a means of controlling the water quality of reactor water, based on the results obtained from the above quantitative analysis method. This water quality control system comprises an electrode housing unit in the electrolytic cell, which is installed in at least one location in said primary cooling system so that the cell comes into contact with reactor water; a signal discharge unit which applies voltage-time wave signals having specified parameters to the working electrode in said electrolytic cell as reference electrode standard voltage; a signal input unit which inputs to the signal discharge unit voltage-time waveform signals having parameters which are determined by the kind of voltammetry utilized, for each chemical species contained in the primary cooling system, and by changing the parameter for each chemical species involved; a storage unit which stores in memory the results of the voltammetry performed according to the signals supplied by the signal discharge unit, in terms of a relationship between electrolysis current and the voltage required to produce the electrolysis current; a current value determination unit which processes the data stored in the storage unit and which determines the limiting current or peak current, according to the kind of voltammetry employed; a concentration computation unit which calculates the concentrations in the reactor water of the desired chemical species, based on the limiting current or peak current values thus determined; and a reactor water control means which regulates the water quality of the reactor water, based on the information produced by the concentration computation unit.

The electrode using unit for an electrolytic cell should be installed in the reactor core, reactor core outlet, or water vapor separator in the reactor. Particularly, it should be installed in the reactor core. If it is installed in the reactor core, it should be installed in an instrumentation column, such as a neutron instrumentation column. Further, in the electrode housing unit in an electrolytic cell, a hydrophobic membrane permeable to gases should be provided; and the dissolved gases in the reactor water should be allowed to come into contact with the electrodes through the gas-permeable membrane, to prevent leakage to the outside world of electrolytic substances, such as potassium chloride, potassium nitrate, and sodium sulfate, which are provided in the electrolytic cell for the purpose of increasing the electrical conductivity of the solution. An example of a hydrophobic gas-permeable membrane that might be used is a membrane made of polytetrafluoroethyene.

Examples of water quality parameters to be controlled by performing quantitative analysis of reactor water are $H_2$ and $O_2$, and the amount of D.K. which is to be injected into the vaporized in the reactor. In a nuclear reactor, it is possible to control the amount of $H_2$ in the reactor after in terms of $H_2$ data, $O_2$ data, $H_2O_2$ data, or by a combination of these 2 or 3 types of data, obtained by quantitative analysis. The amount of $N_2H_2$ to be injected into the vaporizer should be controlled in terms of the $O_2$ concentration data produced by the quantitative analysis.

In a system designed to control the water quality of reactor water, there should be a comparison unit for comparing the results produced by the concentration computation unit of the CPU with standard values. Such a comparison unit should be provided in the CPU.

In the water quality control system under the present invention, the water quality should be regulated by measuring at least one among the variables, the reactor water conductivity, pH, or electric potential, at the sampling point during quantitative analysis of the reactor water, and by taking this information and the dissolved gas information into consideration.

This invention also provides a water quality preventive safety assurance system which comprises a means of performing electrolytically quantitative analysis of reactor water in the primary cooling system of the nuclear reactor, and a means of setting off an alarm when the results obtained by such quantitative analysis means exceed a predefined value. Such a system comprises the following elements: an electrode housing unit for the electrolytic cell, which is installed in at least one location in said primary cooling system so that the cell will come to contact with reactor water; a signal discharge component which applies to the working electrode of the said electrolytic cell voltage-time waveform signals having specified parameters, as reference electrode standard voltage; a signal input unit, which supplies to the signal discharge unit voltage-time waveform signals having parameters according to the kind of voltammetry employed, for each chemical species contained in the primary cooling system, the signal input unit being capable of changing the parameter for each chemical species; a storage unit which stores in memory the results of the voltammetry performed according to the signals supplied by the signal discharge unit, and storing the data in terms of a relationship between the electrolysis current and the voltage required to obtain the electrolysis current; a current value determination unit which processes the data stored in the storage unit and which determines limiting current or peak current values, according to the kind of voltammetry employed; a concentration computation unit which calculates the concentrations in the reactor water of the desired chemical species, based on the determined limiting current or peak current values; a comparison unit which compares the results of said concentration computation unit with standard values; and the aforementioned alarm generator which sets off an alarm when the results produced by the said concentration computation unit, based on the information supplied by the said comparison unit, exceed the standard value.

It is even more desirable that the primary cooling system of the nuclear reactor be provided with a means of measuring the ionic concentrations of $SO_4^{2-}$, $SO_3^{-}$, $Cl^-$, and $Na^+$, which are the decomposition products of chemical resins which are provided for the purpose of cleaning the nuclear reactor; and a means of setting off an alarm when one or more of the said ionic concentrations exceeds the standard value.

Further, this invention comprises an electrode housing unit for the electrolytic cell, which is installed in at least one location in said primary cooling system so that the cell will come into contact with the reactor water; a signal discharge component which applies to the working electrode of the said electrolytic cell voltage-time waveform signals having specified parameters, reference electrode standard voltage; a signal input unit which supplies to the signal discharge unit voltage-time waveform signals having parameters according to the kind of voltammetry utilized, for each chemical species contained in the primary cooling system, the signal input unit being capable of changing the parameter for each chemical species; a storage unit which stores in memory the results of the voltammetry performed according to the signals supplied by the signal discharge unit, and storing the data in terms of a relationship between electrolysis current and the voltage required to obtain the electrolysis current; a current value determination unit which processes the data stored in the storage unit and which determines limiting current or peak current values according to the kind of voltammetry employed; a concentration computation unit which calculates the concentrations of the desired chemical species in the reactor water, based on the determined limiting current or peak current values; and a comparison unit which compares the results of the said concentration computation unit with standard values. This invention also provides an accident forewarning system for the primary cooling system of a nuclear reactor which predicts a potential accident in the primary cooling system, based on the information supplied by the comparison unit.

It is highly desirable that the above-described nuclear reactor water quality control system, reactor water accident prevention system, or the accident prediction system be provided with a monitoring system to ensure that the signal input unit, signal supply unit, concentration computation unit, and comparison unit are working properly. As an additional feature, in the event of a malfunction detected by the monitoring system, the system should be able to set off an alarm.

Any input of signals generated by the signal input unit to the signal discharge unit should be performed via a function generator.

Among the prior arts relating to water quality assurance for nuclear reactors is a method, published in Japanese Patent Kokai (Laid-open) No. 61-148394, for reducing the concentration of radioactive species in the reactor water by controlling the concentrations of nickel and cobalt ions in the water supply in such a way that the concentrations will be higher at the beginning of a reactor operation, declining gradually with the passage of time, according to their concentration change curves. However, there is no mention in the said reference material of in situ quantitative analysis of chemical species such as $H_2$, $O_2$, and $H_2O_2$ found in the cooling water system, or a method of controlling the water quality by feeding the analytical information back to the control system.

Among the known nuclear power plant problem diagnosis systems is one published in Japanese Patent Kokai (Laid open, No. 60-238791) this compares with boundary values the deviation of data collected from the plant from the output values obtained by entering the data into a reference model, so as to automate the process of identifying the type of breakage that has occurred, based on codes generated by the model.

Concerning plant emergency operation support equipment, Japanese Patent Kokai (Laid open No. 61-164194) describes a system consisting of a detector for measuring the process quantity of a plant, a monitoring device for checking the conditions of multiplexed pieces of equipment, three evaluation methods, and display units, for reducing the workload on the operating personnel.

Adequate methods for quantitatively analyzing the concentrations of $H_2O_2$, $O_2$, and $H_2$ are necessary in many fields, especially for controlling the corrosive environment prevailing in nuclear reactor water cooling systems. Among the existing arts for measuring the concentration of $H_2O_2$ is, as described in Japanese Patent Kokai (Laid open) No. 55-146035, a method of electrolyzing an aqueous solution of $H_2O_2$ under constant cathode voltage, and determining the concentration of $H_2O_2$ by measuring the resulting electrolysis current. However, in cases where both $O_2$ and $H_2O_2$ are present, the electrolysis current observed under this method will contain the current component due to $O_2$ as well that due to $H_2O_2$. Thus, the method is incapable of determining the concentration of $H_2O_2$ alone. Among the devices intended to determine the concentration of $H_2O_2$ alone. Among the devices intended to determine the concentration of $H_2O_2$ in the presence of $O_2$ is one described in Japanese Patent Kokai (Laid Open) No. 56-37549. This device removes the effect of oxygen by dipping both an oxygen detector and an auxiliary oxygen detector in the test solution. However, since this device contains an oxygen-permeable membrane and a hydrogen peroxide decomposition membrane, its analytical performance can be significantly affected by the surrounding environment. At any rate, it cannot be used in high-temperature, high-pressure nuclear reactor cooling water.

Quantitative analysis devices for the analysis of $O_2$ or $H_2$, amenable to use under high-temperature, high-pressure conditions, have been developed, such as the devices described in Japanese Patent Kokai (Laid open) Nos. 59-174748 and 59-3345. However, these devices cannot handle the quantitative analysis of $O_2$ or $H_2$ in solutions in which $H_2O_2$ occurs together with $O_2$ or $H_2$.

To achieve in situ analysis of the water quality of the nuclear reactor water and to control water quality, a technique for simultaneous quantitative analysis of $O_2$, $H_2$, and $H_2O_2$ is essential. A survey of existing reactor water monitoring techniques, even if the survey is narrowly focused on this requirement, indicates that no such techniques exist in the public domain, as discussed above.

The electrolysis currents, measured by running several types of pulse voltammetry using different voltage-time waveform signals, are given in different function forms. Therefore, the diffusion limiting current values and peak current values of a current/voltage curve, consisting of additive electrolysis current components of the several types of the substances to be measured, measured in different pulse electrolysis modes, can be expressed for each pulse mode as independent equations whose unknown variables are the concentrations of the target substances. Therefore, the concentrations of these substances can be determined by solving these equations by treating them as a set of simultaneous equations.

Through execution of multiple voltammetries, a voltammetry device, especially pulse voltammetry device, which is connected to a computer is capable of performing simultaneous in situ quantitative analysis of multiple chemical species present in a reactor water system. Such a device can also print or display the analytical results to present the results of water quality tests in clear format to human operators, thus helping humans to monitor the water quality.

The said voltammetry instrument system can compare previously entered standard values for various chemical species with the results of simultaneous in situ quantitative analyses by using a computer, and based on this comparison, can feed gases and chemical species rapidly and accurately into the reactor in order to adjust its water quality. In this manner, the device performs water quality control.

DESCRIPTION OF THE PREFERRED EMBODIMENTS

[Examples]

The following explains this invention further in reference to its embodiments; however, this invention is not limited to the embodiments given below.

Example 1

Example 1 illustrates the location of installation of a tri-electrode system in a BWR nuclear reactor pressure vessel, the configuration of the tri-electrode system, an analytical system, a water quality control system, a safety diagnosis system, analysis implementation examples, and the underlying principles of analyses.

Figure 1:
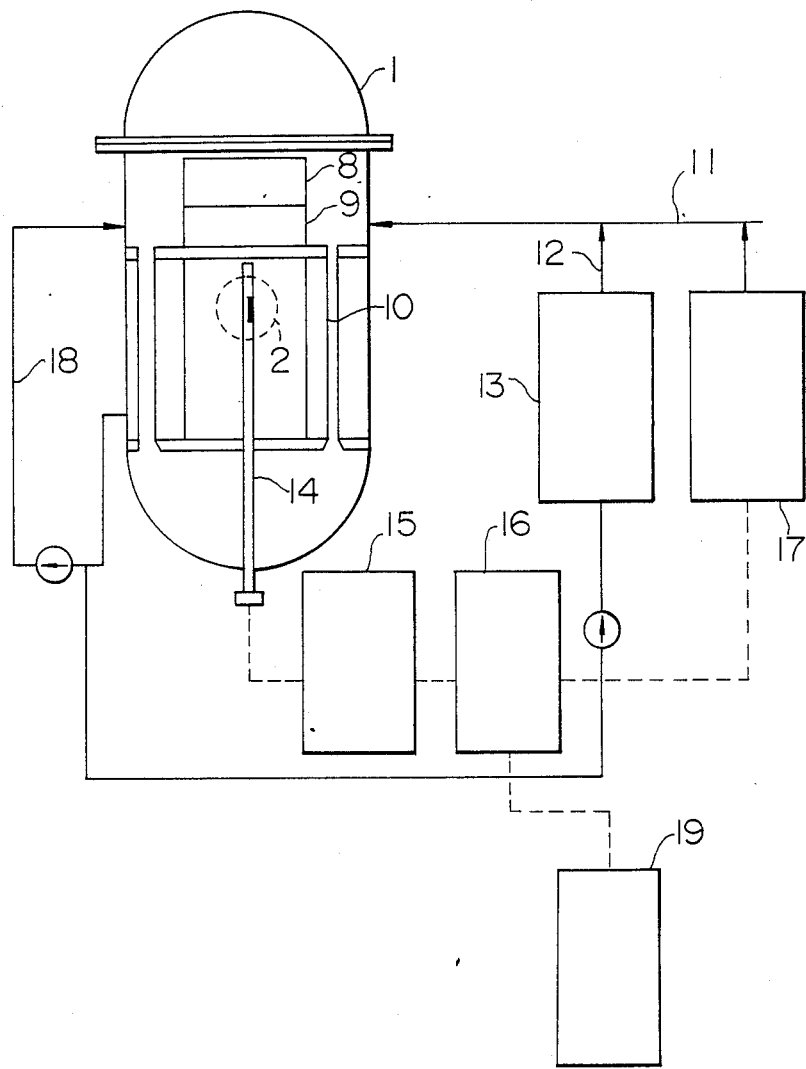
FIG. 1 is a schematic configuration diagram showing a BWR plant water quality control system containing a tri-electrode system inside instrumentation columns.
Figure 14:
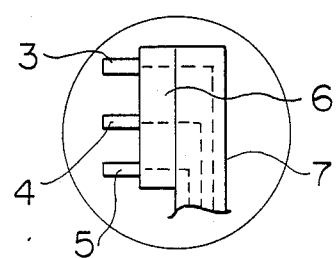
FIG. 14 is an enlarged view of the electrode housing unit shown in FIG. 1.

FIG. 1 shows the peripheral structural constituent elements in BWR nuclear reactor pressure vessel 1 in Example 1. FIG. 14 shows an enlarged view of the electrode housing unit. Electrode housing unit 2 of the tri-electrode system is inserted into reactor instrumentation column 14, and is into contact with the reactor water inside reactor core 10. The reactor instrumentation column 14 into which the tri-electrode system is inserted has an opening inside reactor core 10; the electrodes are inserted into the column in double structure. After the insertion, the neutron instrumentation inner column 7 into which the tri-electrode system is inserted serves to shield the reactor water from the outside world. Number 3 represents a counter electrode; 4 represents a working electrode, also known as a monitor electrode; 5 represents a reference electrode; and 6 represents an electrode support, which is an insulator. Monitor electrode 4 is operated by a potentiostat, electrochemical interface 15, and CPU 16 (a computer CPU and an auto-control unit). Analytical results are transmitted to a remote control command system and analytical results display unit 19.

The analytical results are compared in CPU 16 with previously entered standard values, and based on this comparison CPU 16 sends instructions to the control system in gas/chemical injection system 17 to cause valves to be opened and closed. By repeating this process, CPU 16 regulates the water quality.

Monitor electrode 4 can be either a plate electrode, microelectrode or wire-type needle electrode, which is on the same plane as electrode support 6 is; the monitor electrode can be made in any shape and with any material. Reference electrode 5 may be a saturated calomel electrode (SCE), standard hydrogen electrode (SHE), or silver chloride-silver electrode (Ag-AgCl) and connection conditions of electrical circuits and interface bus lines.

In pressure vessels in nuclear reactors, $H_2$, $O_2$, and $H_2O_2$ gases are generated when radiation decomposes water. Most of such gas generation occurs in the nuclear core. Therefore, in controlling the gas formation reactions so as to control the water quality, the capability of a water quality control system can be improved by conducting water quality analysis directly inside the nuclear core. And for maintenance checks on electrodes, the electrode can be removed from the nuclear core instrumentation columns.

As with the case of the above in-reactor instrumentation column, electrodes can be installed on drier, separator 9, radiation test piece insertion instruments, and other removable equipment and parts, so that the electrode can be installed inside the nuclear reactor pressure vessel. Also, they can be installed directly on the walls of the pressure vessel.

As a variation of this embodiment, flangings can be installed directly inside nuclear reactor recirculation pipe 18, or the reactor water can be routed to a sampling pipe, and electrodes can be attached to the sampling line, thus ensuring the measurement of water quality. Although electrodes attached at such locations take more time to detect the reaction products generated inside the reactor core, for the purpose of controlling the contents of impurities circulating in the primary cooling system they offer sufficient measurement accuracy. The most general application of these monitoring systems would be to attach them all over the components such as nuclear reactor water supply pipe 11, nuclear reactor cleaning system 12, and around nuclear rector cleaning and desalinization equipment 13, rather than attaching them in the rector core or in flangings only, so as to manage and control the water quality and to detect potential leaks of the cooling water, thus providing a comprehensive, total water quality control and safety diagnosis system.

Similarly, electrodes can be installed in a boiling water reactor (BWR) or inside the secondary vaporizer of a pressurized water reactor (PWR), or in the boilers in thermal plants.

Figure 2:
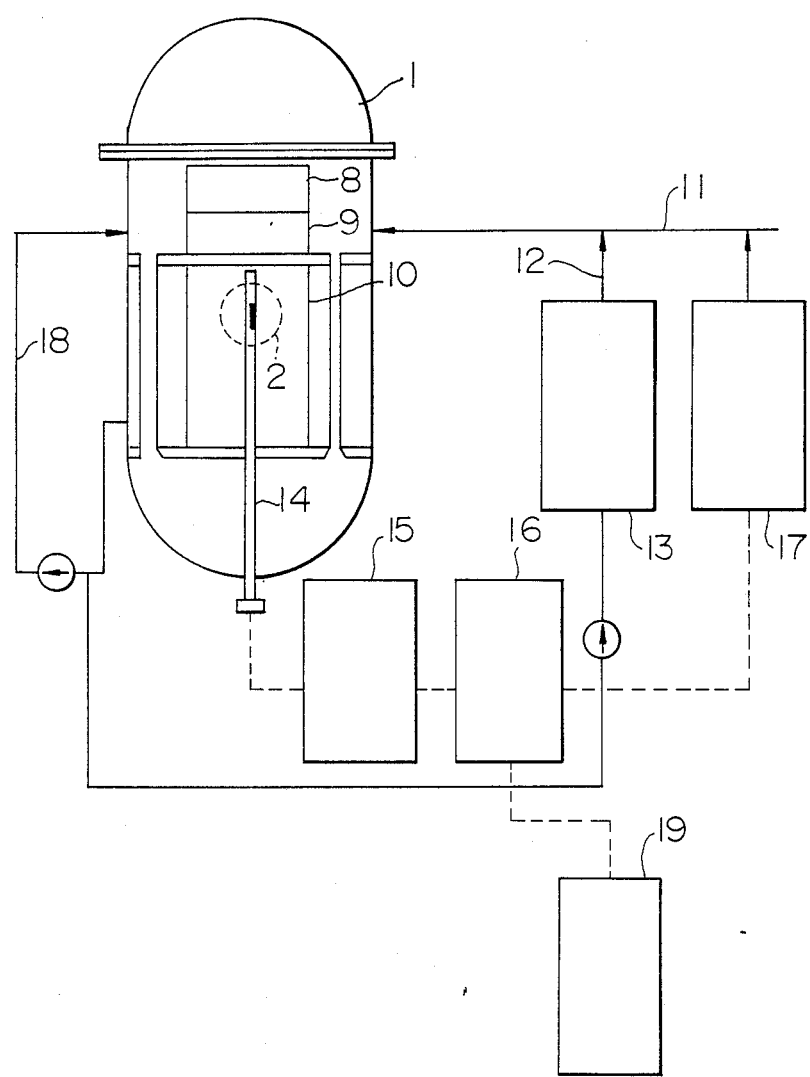
FIG. 2 is a schematic configuration diagram showing a BWR plant water quality control system containing a tri-electrode system in an electrolytic cell which is provided with permeable membranes and which is installed in an instrumentation column.
Figure 15:
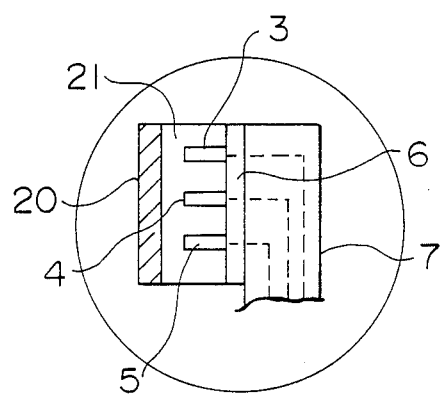
FIG. 15 is an enlarged view of the electrode housing unit shown in FIG. 2.
Figure 16:
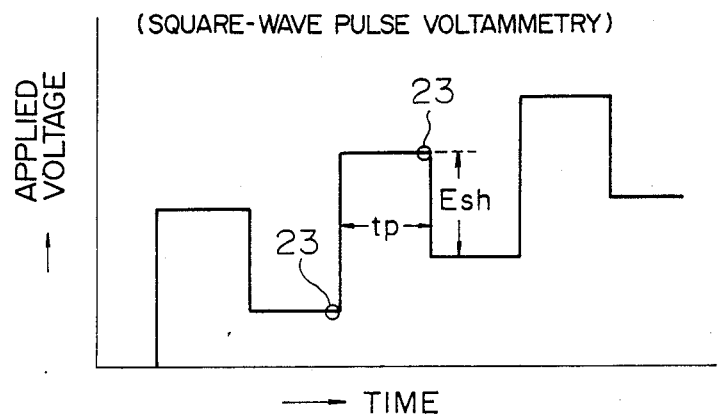
FIGS. 16–19 are applied signal waveforms of the various voltammetries.
Figure 17:
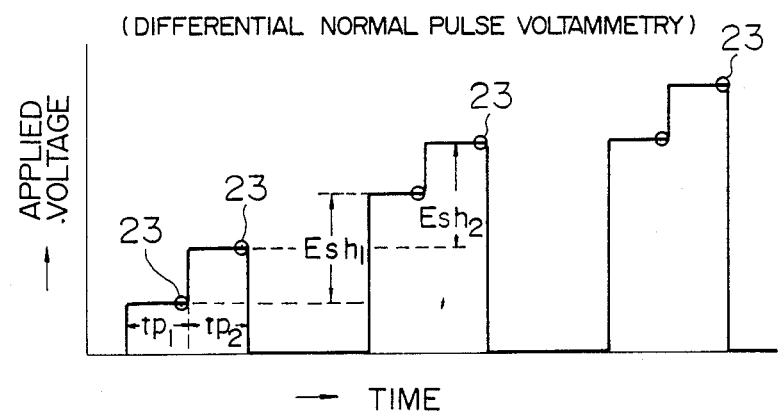
Figure 18:
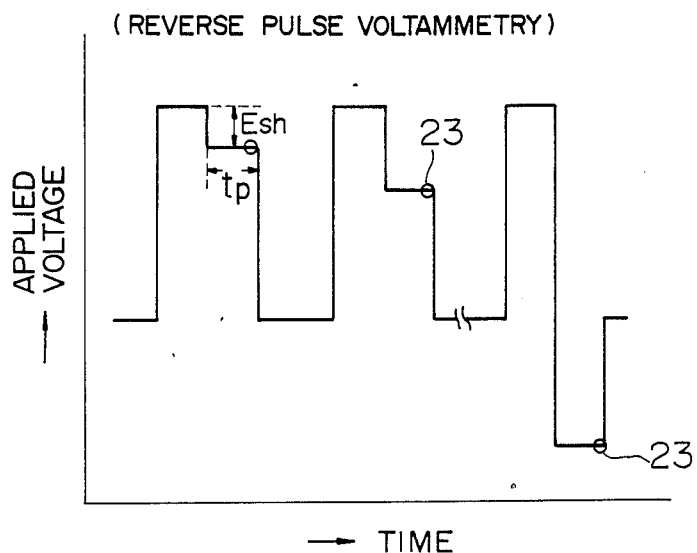
Figure 19:
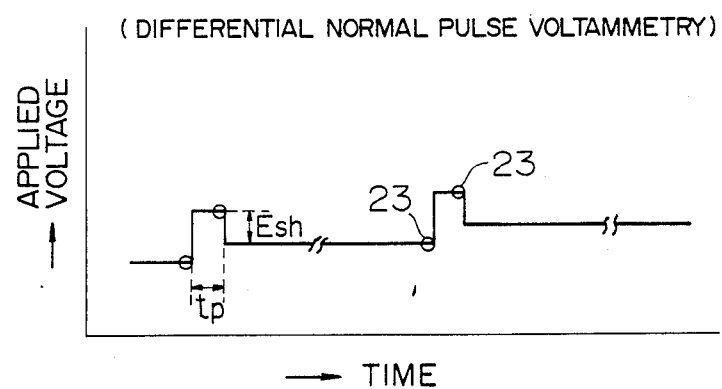

In FIG. 2, electrode housing unit 2 consists of an electrolytic cell provided with permeable membranes which have hydrophobic gas-permeable membrane 20. Sealed in the cell is dilute electrolytic solution 21. FIG. 15 shows an enlargement of the electrode housing unit. Use of this cell facilitates electrochemical measurements.

Figure 3:
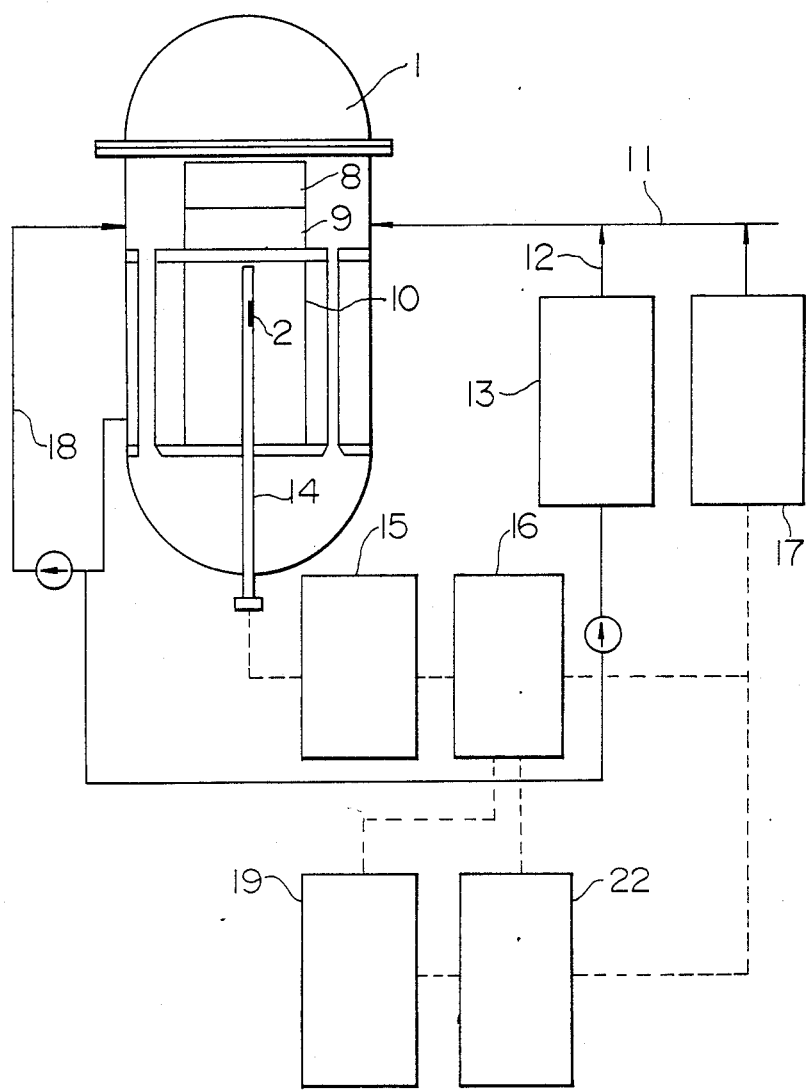
FIG. 3 is a schematic configuration diagram of a BWR plant water quality control system equipped with a safety diagnosis system.

In FIG. 3, the BWR reactor consisting of the electrodes and electrolytic cell used in FIGS. 1 and 2, to which control monitoring system 22 for monitoring the water quality control system has been added. Control monitoring system 22 has at least one computer/CPU. These computers determine whether or not CPU 16, for controlling the water quality control system, and electrochemical interface 15 are operating properly, in order to ensure the reliability and stability of the water quality control system. For detecting an abnormal operation, signals from the water quality control system consisting of electrochemical interface 15, CPU 16, and gas/chemical injection system 17 are return to a dummy circuit, and the criterion employed for detecting the presence of an abnormal operation is based on the determination whether or not the results of computation, analysis, and control are within specified values and specified precision.

Figure 4:
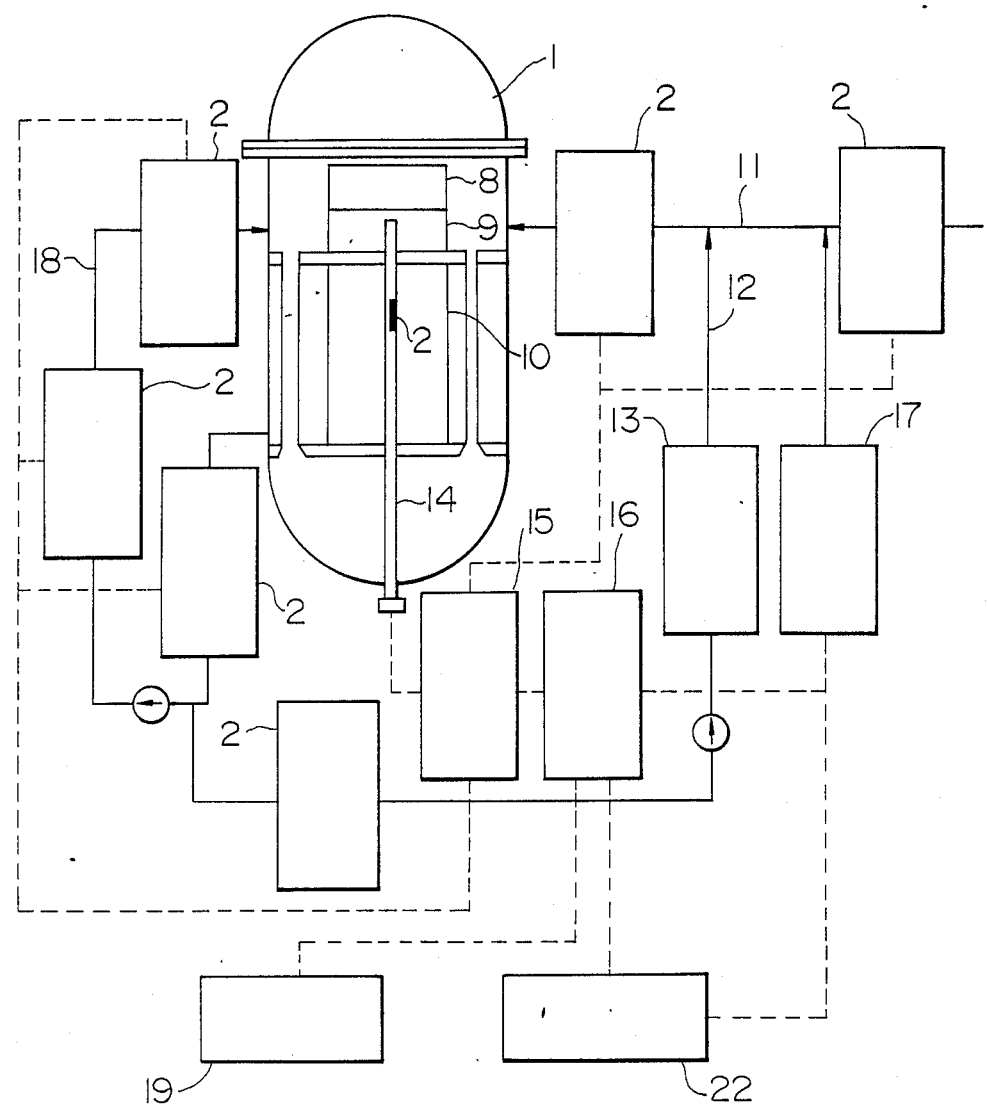
FIG. 4 is a schematic configuration diagram of a BWR plant water quality control system, in which water quality monitors are provided in various locations.

FIG. 4 is a comprehensive water quality control system consisting of all the constituent elements depicted in FIGS. 1 through 3. Specifically, in this control system electrode housing units 2 are distributed in the reactor, water supply system, circulation system, and cleaning system; and the control system performs water quality controls based on the analysis of water quality at these various locations. Especially, during a water leak accident it is useful to detect any abnormality in the concentration of dissolved $O_2$ at these various locations.

Figure 5A:
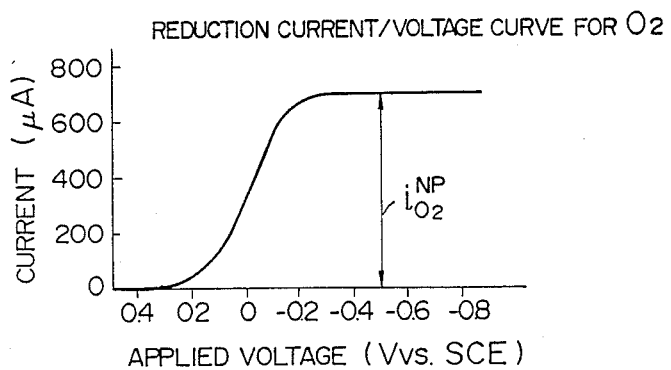
FIG. 5 (a) is a reduction current/voltage curve of $O_2$, using normal pulse voltammetry. Similarly, FIG. 5 (b) is a reduction current/voltage curve of $H_2O_2$. Also similarly, FIG. 5 (c) is a reduction current/voltage curve of $O_2$ and $H_2O_2$, whose concentrations are equal to those shown in FIGS. 5 (a) and (b).
Figure 5B:
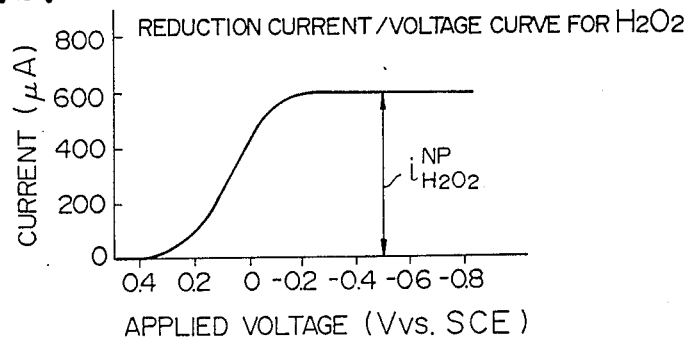
Figure 5C:
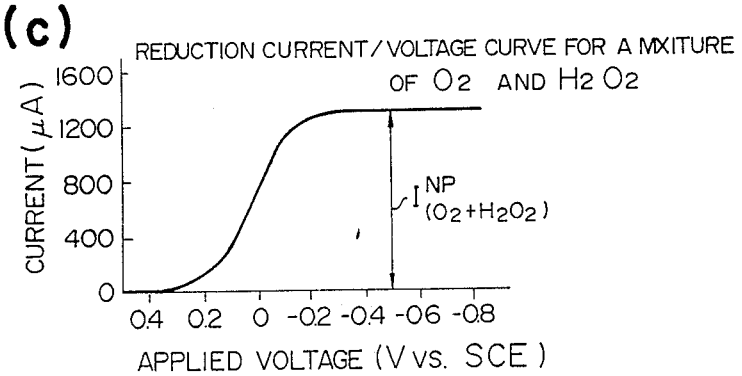
Figure 6:
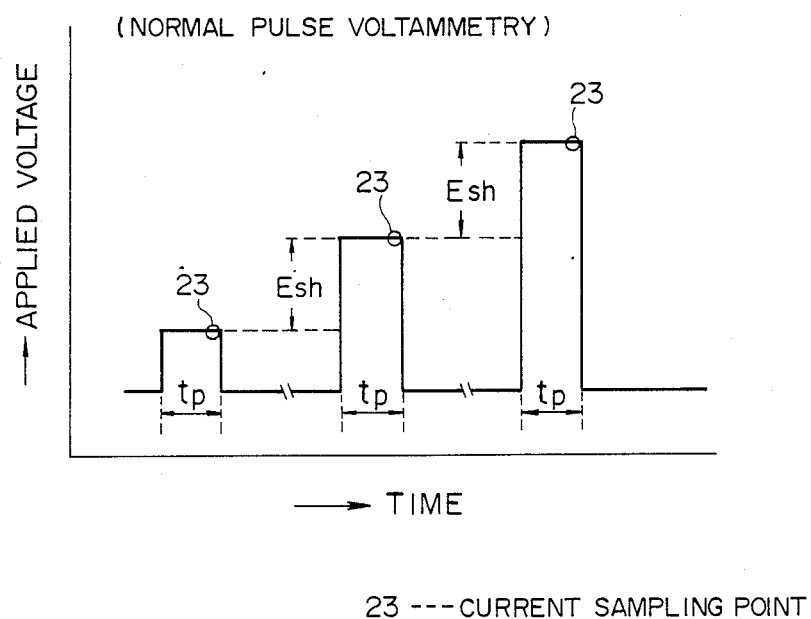
FIG. 6 is an applied signal waveform diagram for normal pulse voltammetry.

FIG. 5 (a) is a reduction current/voltage curve of $O_2$, measured by using the normal pulse voltammetry mode. Similarly, FIG. 5 (b) is a reduction current/voltage curve of $H_2O_2$, measured by using the normal pulse mode. FIG. 5 (c) is a normal pulse voltammogram in the direction of reduction of primary cooling water solution, containing $O_2$ and $H_2O_2$ of the same concentrations as the concentrations of $O_2$ and $H_2O_2$ measured in (a) and (b), where the horizontal axis represents applied voltage. As shown in the normal pulse signal waves in FIG. 6, the applied voltage is applied and sweep in pulses, with an applied step width of Esh relative to the reference electrode, where tp denotes the pulse width. Each of the vertical axes in FIG. 5 represent electrolysis current which was observed relative to the different pulse-like applied voltages. The electrolysis current is sampled at final step 23 of pulse width tp of the normal pulse voltammetry shown in FIG. 6.

$i_{O_2}^{NP}$ shown in FIG. 5 (a) is the limiting current value for reducing $O_2$, while $i_{H_2O_2}^{NP}$ shown in FIG. 5 (b) is the limiting current value for reducing $H_2O_2$. $I_{(O_2+H_2O_2)}^{NP}$ in FIG. 5 (c) is the limiting current for simultaneously reduction of $O_2$ and $H_2O_2$. These 3 current/voltage curves were measured by using a platinum disc electrode as monitor electrode 4. FIG. 5 (a) was measured by using a solution containing $O_2$ but not $H_2O_2$.

FIG. 5 (b) was measured by using a solution containing H₂O₂ but not O₂. FIG. 5 (c) was measured by using a solution containing both H₂O₂ and O₂.

Limiting current value $I_{(O2+H2O2)}^{NP}$ in FIG. 5 (c) is given as a sum of electrolysis current components $i_{O2}^{NP}$ and $i_{H2O2}^{NP}$ of O₂ and H₂O₂, respectively.

$$I_{(O2+H2O2)}^{NP} = i_{O2}^{NP} + i_{H2O2}^{NP} \quad (1)$$

Generally, $i_{O2}^{NP}$ and $i_{H2O2}^{NP}$ can be given by the following equations, respectively:

$$i_{O2}^{NP} = f(n_{O2}, D_{O2}, tp)c_{O2} \quad (2)$$

$$i_{H2O2}^{NP} = f(n_{H2O2}, D_{H2O2}, tp)C_{H2O2} \quad (3)$$

where $n_j$, $D_j$, and $C_j$ (j denoting either O₂ or H₂O₂) represent the total number of reacting electrons involved in a reduction reaction, diffusion coefficient, and concentration in the solution of O₂ and H₂O₂, respectively. tp represents the pulse width. f(nj, Dj, tp) is given by the following equation:

$$f(n_j, D_j, tp) = n_j FA(D_j/\pi tp)^{\frac{1}{2}} \quad (4)$$

where F denotes the Faraday constant, A the electrode surface area of the monitor electrode, and $\pi$ the ratio of the circumference of a circle to its diameter. Substituting Equations (2) and (3) into Equation (1), we obtain $$I_{(O2+H2O2)}^{NP} = f(n_{O2}, D_{O2}, tp)C_{O2} + f(n_{H2O2}, D_{H2O2}, tp)C_{H2O2} \quad (5)$$

Therefore, the normal pulse voltammetry in the reducing direction of a solution containing both O₂ and H₂O₂ of unknown concentration gives the current/voltage curve of the form shown in FIG. 5 (c), and the observed diffusion limiting current can be expressed in Equation (5), where $I_{(O2+H2O2)}^{NP}$ denotes the observed diffusion limiting current, and f(nj, Dj, tp) represents a function which can be defined when the experimental conditions employed are known. Therefore, Equation (5) turns out to be a two-dimensional first order equation containing two unknown variables, $C_{O2}$ and $C_{H2O2}$.

The peak current value $I_{(O2+H2O2)}^{DP}$ which is measured by differential pulse voltammetry for the reduction of a solution containing both O₂ and H₂O₂ of unknown concentrations is given by the following equation:

$$I_{(O2+H2O2)}^{DP} = g(n_{O2}, D_{O2}, tp, \ldots)C_{O2} + g(n_{H2O2}, D_{H2O2}, tp \ldots)C_{H2O2} \quad (6)$$

As discussed in the Journal of Electroanalytical Chemistry, 175 (1984) pp. 1–13, g(nj, Dj, tp, ...) represents a family of functions entirely different from equation (4) containing f(nj, Dj, tp). Thus, the measured peak current value $I_{(O2+H2O2)}^{DP}$ in clearly different from $I_{(O2+H2O2)}^{NP}$.

Since g(nj, Dj, tp, ... ) is determined by setting measurement parameters and experimental conditions, Equation (6) constitutes a two-dimensional first-order equation independent of Equations (5), containing the unknown variables $C_{O2}$ and $C_{H2O2}$. Therefore, the solutions $C_{O2}$ and $C_{H2O2}$ of the set of linear equations (5) and (6) is given by the following equations:

$$C_{O2} = \frac{\begin{vmatrix} I_{(O2+H2O2)}^{NP} & f(n_{H2O2}, D_{H2O2}, tp) \\ I_{(O2+H2O2)}^{DP} & g(n_{H2O2}, D_{H2O2}, tp, \ldots) \end{vmatrix}}{\begin{vmatrix} f(n_{O2}, D_{O2}, tp) & f(n_{H2O2}, D_{H2O2}, tp) \\ g(n_{O2}, D_{O2}, tp, \ldots) & g(n_{H2O2}, D_{H2O2}, tp, \ldots) \end{vmatrix}} \quad (7)$$

$$C_{H2O2} = \frac{\begin{vmatrix} f(n_{O2}, D_{O2}, tp) & I_{(O2+H2O2)}^{NP} \\ g(n_{O2}, D_{O2}, tp, \ldots) & I_{(O2+H2O2)}^{DP} \end{vmatrix}}{\begin{vmatrix} f(n_{O2}, D_{O2}, tp) & f(n_{H2O2}, D_{H2O2}, tp) \\ g(n_{O2}, D_{O2}, tp, \ldots) & g(n_{H2O2}, D_{H2O2}, tp, \ldots) \end{vmatrix}} \quad (8)$$

Consequently, if there is an overlap between the current/voltage curves of two kinds of measured substances of unknown concentrations, their concentrations can be determined by the above method by measuring the electrolysis current values by using two kinds of voltammetry, necessary for setting up two independent equations. It follows, then, that if 3 kind, 4 kind, or 5 kind of substances to be measured are electrolyzed in approximately the same voltage range, and if their electrolysis current components are observed as overlapping values, by combined use of 3 to 5 kinds of voltammetries, the concentrations of the individual measured substances can be determined.

These analytical processes are handled in potentiostat-electrochemical interface 15 and CPU 16 (computer CPU and auto-control unit), and water quality control is achieved by comparing these analytical results with the standard values and controlling the gas/-chemical injection system 17.

Of the various pulse voltammetries, those which can be obtained from limiting current values include reverse pulse voltammetry, in addition to normal pulse voltammetry.

Those which can be obtained from peak current values include differential normal pulse voltammetry and square-wave pulse voltammetry, in addition to differential pulse voltammetry.

FIGS. 16–19 show the voltage-time waveform signals for various pulse voltammetries.

Example 2

Example 2 is designed to study appropriate reactor water quality management conditions by use of low distortion speed stretching tests, in order to study the limiting voltage and limiting electric conductivity at which stress corrosion cracking (SCC) ceases to occur; using the data thus obtained, in this embodiment the reactor water environment is controlled with a system shown in FIGS. 1 through 4 in order to inhibit the occurrence of SCC.

Figure 7:
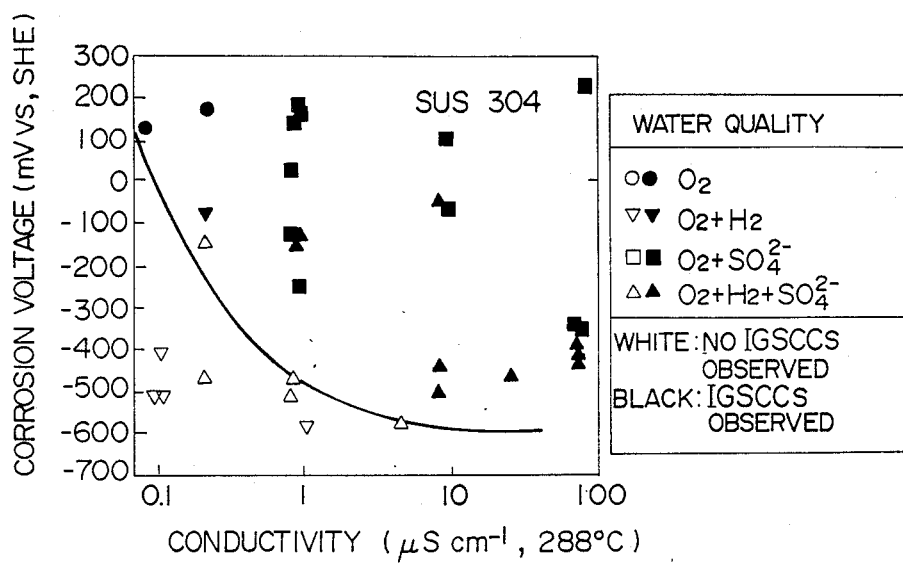
FIG. 7 is a characteristic diagram showing the influence of impurities on sensitized SUS304 steel, as determined by SSRT tests.

FIG. 7 shows the relationship between the sensitivity of SUS304 steel to SCC under the real reactor water environment, to which no hydrogen is supplied, the corrosion voltage, and the electric conductivity. In the figure, "X" indicates the condition under which the occurrence of SCC was observed; "o" indicates the condition under which no SCC was observed. As can be seen in FIG. 7, the higher the corrosion voltage and the higher the electric conductivity, the greater is the likelihood of occurrence of an SCC.

To prevent the occurrence of SCC, in this invention the water quality conditions of the reactor water and of the primary cooling water system, especially $H_2$ gas concentrations and their relationship to water quality, were controlled by constant monitoring, so that the corrosion voltage and the conductivity remain in the SCC-inhibiting region lying below the curve shown in FIG. 7.

Figure 8:
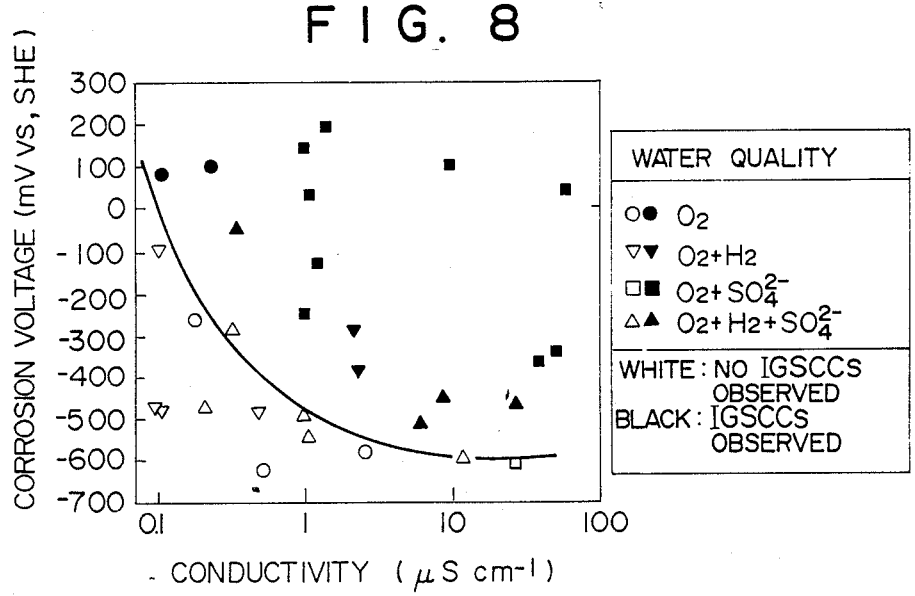
FIG. 8 is a characteristic diagram showing the influence of impurities on sensitized SUS316 steel, as determined by SSRT tests.

FIG. 8 shows the relationship between the sensitivity of SUS316 steel to SCC, the corrosion voltage, and the electric conductivity, under the same real reactor water environmental conditions as those described above. For comparison, the figure also provides the relationship between the limiting voltage and the limiting electric conductivity of SUS304 steel (solid line). As is evident from FIG. 8, the limiting line at which SCC ceases to occur in SUS316 steel is in agreement with the limiting line at which SCC ceases to occur in SUS304 steel. SUS316 steel has the same SCC-inhibiting region as SUS304 region. Thus, it is demonstrated that the occurrence of SCC in SUS304 or SUS316 can be inhibited by using the same water quality control conditions.

Example 3

For determining the best water quality conditions, this embodiment was intended to evaluate the region in which SCC is likely to occur, using the concentrations of oxygen and hydrogen peroxide in the reactor water as parameters.

Figure 9:
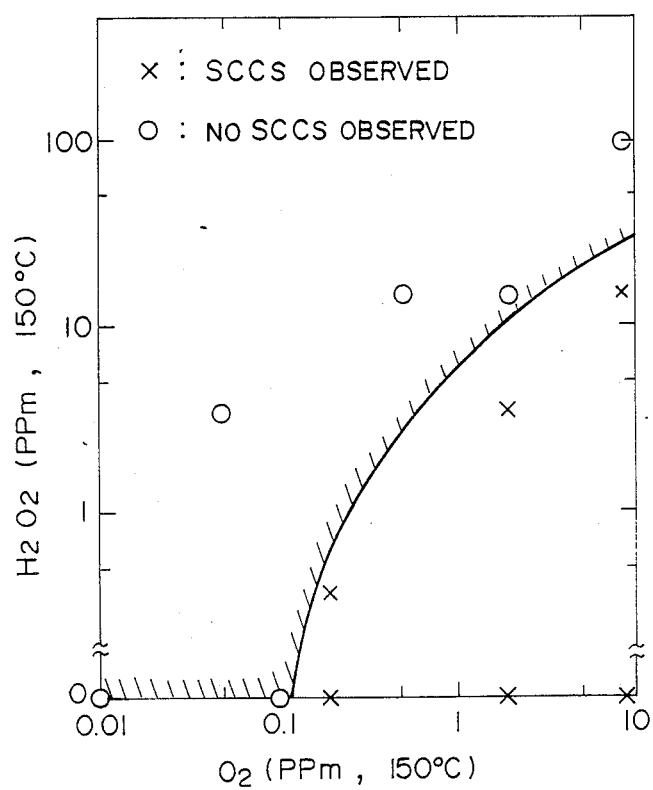
FIG. 9 is a correlational graph showing the IGSCC sensitivity of $H_2O_2$—$O_2$ at 150° C.

FIG. 9 shows an $H_2O_2$- $O_2$ correlation graph, indicating the sensitivity of structural materials to inter granular stress corrosion cracking (IGSCC) at 150° C. In FIG. 9, "x" indicates the occurrence of IGSCC; "o" indicates the absence of IGSCC. As is evident from FIG. 9, in regions in which the concentration of dissolved oxygen is higher than 0.1 ppm, the critical concentration of hydrogen peroxide necessary to inhibit the occurrence of IGSCC increases as the concentration of dissolved oxygen increases. Thus, it is clear that when a solution contains different chemical species dissolved in it, its SCC propensity cannot be evaluated on the basis of corrosion voltage alone. In view of this fact, this embodiment, as shown in the preceding Embodiment 2, sets the corrosion voltage and conductivity in a range which inhibits the occurrence of IGSCC; and uses a system of the configuration shown in FIGS. 1 through 4, to constantly monitor $H_2O_2$, $O_2$, and $H_2$ so that the concentrations of $H_2O_2$ and $O_2$ will be kept within a range that inhibits the occurrence of IGSCC, in order to control the water quality to prevent the IGSCC of materials.

Example 4

The purpose of Example 4 was to study the influence of the pH on SCC in order to identify optimal water quality conditions.

Figure 10:
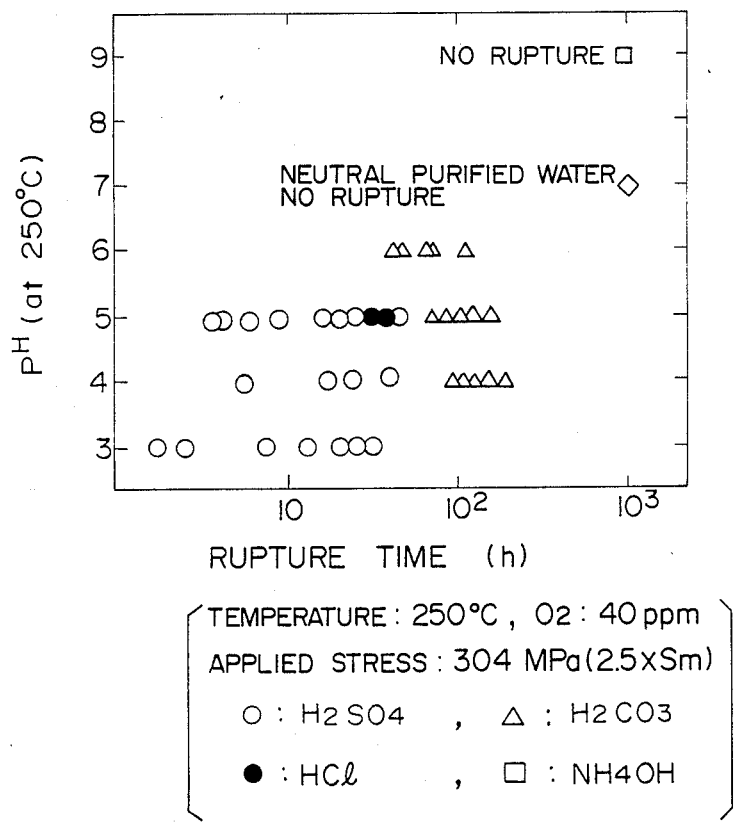
FIG. 10 is a characteristic diagram showing the influence of the pH and anions on the IGSCC of sensitized SUS304 steel in hot water containing oxygen.

FIG. 10 shows the influence of the pH and anions on the IGSCC of sensitized SUS304 steel in hot water containing 40 ppm of oxygen. When the pH is adjusted using sulphuric acid and ammonia water, in the neighborhood of pH 5, the amount of time which a material takes before cracking is exceedingly short. In low pH regions, anions such as sulphuric acid and salts show the same degree of corrosiveness relative to IGSCC; by contrast, carbonic acid shows low corrosiveness. Therefore, in this invention, when judged solely on the basis of the relationship between the pH and IGSCC, the occurrence of IGSCC can be prevented by maintaining a high pH, as indicated in the figure.

Example 4 demonstrates that the occurrence of IGSCC can be prevented by adjusting the pH of the solution to the 7-7.5 range, using the system of the present invention.

Example 5

This Example was intended to study, using the techniques developed in this invention, the influence of corrosion voltage on the speed of fracture, in order to control the water quality, based on the data thus obtained, so as to ensure a system having optimal corrosion voltage.

Figure 11:
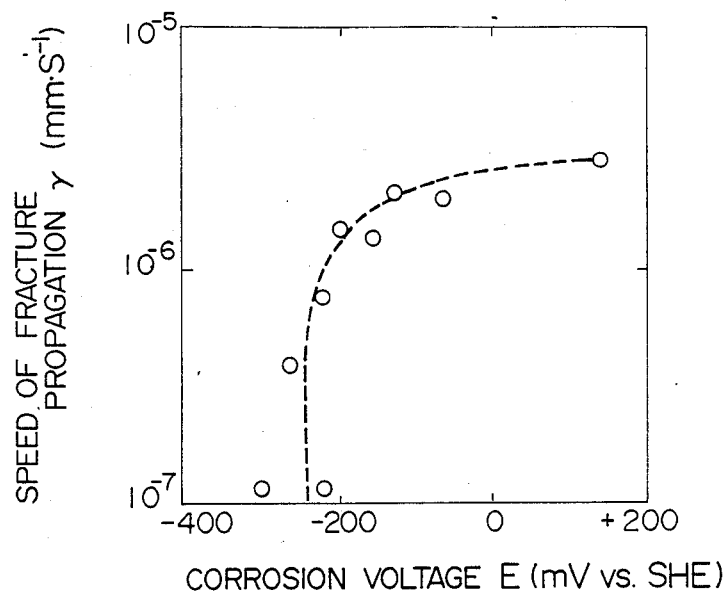
FIG. 11 is a characteristic diagram showing the influence of corrosion voltage on the speed of fracture in sensitized SUS304 steel.
Figure 12:
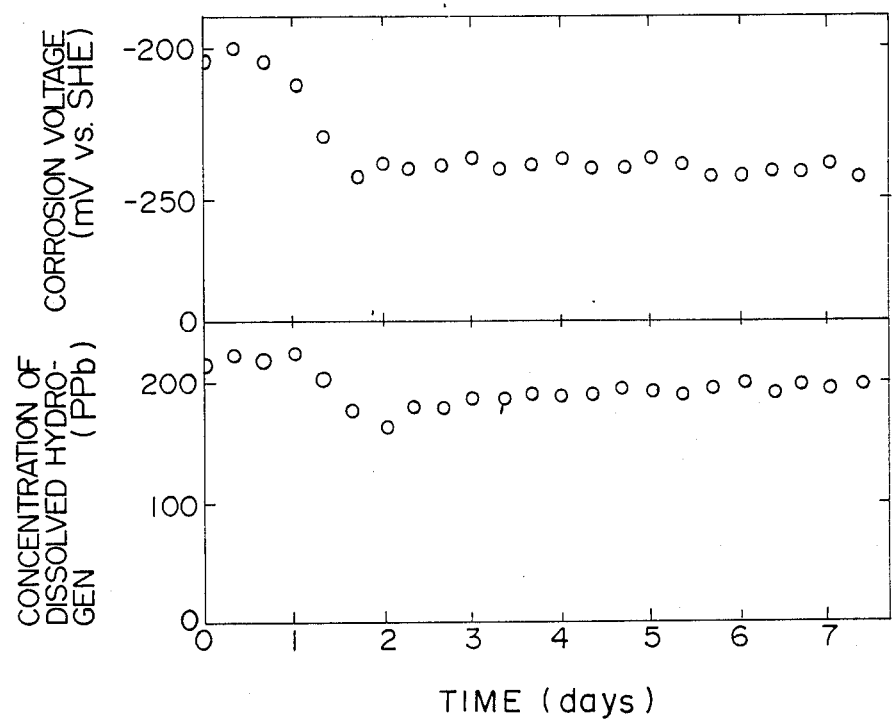
FIG. 12 is a characteristic diagram showing the time dependencies of corrosion voltage and dissolved hydrogen concentration which are regulated by an $H_2$ injection control system.

FIG. 11 shows the results of evaluating the influence of corrosion voltage on the speed of fracture development in sensitized SUS304 steel. When the corrosion voltage is set below $-230$ mV vs. SHE, the speed of fracture development becomes exceedingly slow, virtually eliminating SCC. FIG. 12 shows the results of controlling this system to maintain a corrosion voltage of less than $-230$ mV by supplying $H_2$ gas from gas/chemical supply system 17. The corrosion voltage was controlled by controlling the amount of dissolved hydrogen, using the system of the present invention.

Since the corrosion voltage falls below $-230$ mV if the quantity of dissolved hydrogen under a steady state is maintained in the 150-200 ppb range, the quantity of hydrogen was maintained in this range by feeding back the observed concentration of dissolved $H_2$ to the system and by regulating the amount of hydrogen gas which was blown into the solution from gas/chemical supply system 17.

Example 6

In this Example 6, the water quality control system shown in FIGS. 1 through 4 was used to achieve comprehensive water quality control by monitoring the above-described dissolved $O_2$ concentration, $H_2O_2$ concentration, pH, corrosion voltage, conductivity, and dissolved $H_2$ concentration.

By controlling the water quality parameters to maintain the optimal water quality conditions shown in Embodiment 5 above, such as dissolved $O_2$ concentration, 10-50 ppb; $H_2O_2$ concentration, 10-50 ppb; pH, 7-8; corrosion voltage, $-230$ mV vs. SHE or lower; and dissolved $H_2$ concentration, 150-200 ppb; we succeeded in constructing a system capable of achieving an overall reduction in the amount of corrosion and prevention of IGSCC.

Figure 13:
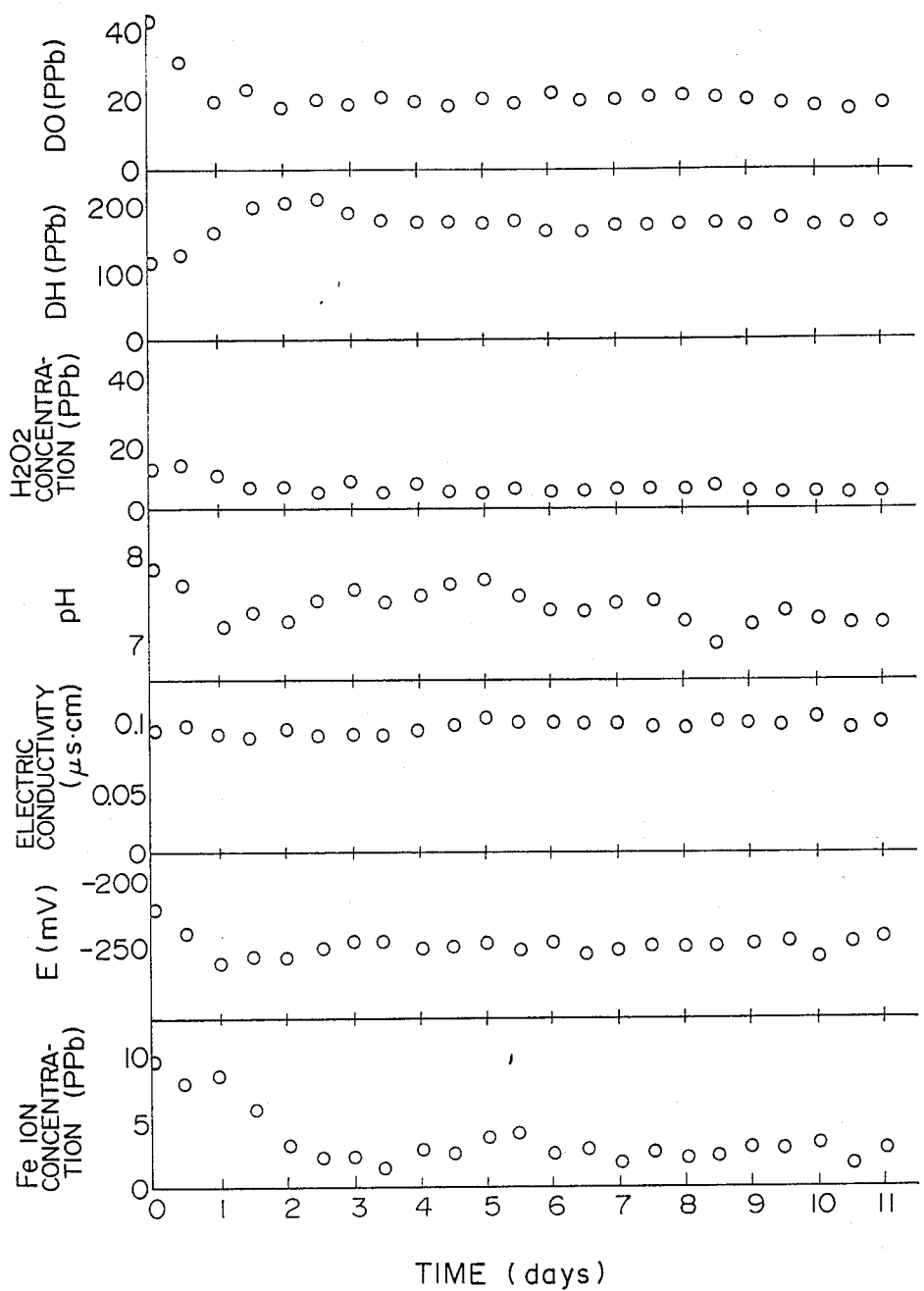
FIG. 13 is a characteristic diagram showing the time dependencies of the dissolved $O_2$, dissolved $H_2$, dissolved $H_2O_2$, iron ion concentration, pH conductivity, and corrosion voltage, which are regulated by a water quality control system.

FIG. 13 shows the results of monitoring and controlling the concentrations of dissolved $O_2$, $H_2O_2$, and dissolved $H_2$; pH; corrosion voltage; conductivity; and the concentration of iron ions; using the present water quality control system during operation of a simulated nuclear power plant. All values are within the range of optimal conditions, namely, the water quality conditions satisfying the standard values, confirming that the system was operating properly. The concentration of iron ions detected by the in situ simultaneous quantitative analysis equipment system was below 5 ppb.

EFFECTS OF THE INVENTION

This invention allows simultaneous quantitative in situ analysis of various chemical species found in the cooling water system and the reactor water in a nuclear power plant, allowing on-the-spot water quality monitoring of the reactor water and cooling system.

Further, the invention allows an overall evaluation of water quality by relating the water quality monitoring, analytical results, and the pH, voltage, and electric conductivity of the reactor water and at various locations of the water cooling system.

Further, the above effects are integrated with a computer and computation processing system, allowing fast, accurate, automated water quality control.

What is claimed:

1. A quantitative analysis method for analysis of reactor water in a nuclear reactor which comprises the process for contacting three electrodes of a working electrode, a counter electrode, and a reference electrode in an electrolytic cell with the reactor water in at least one location in the primary water-based cooling system in a nuclear reactor; a process for electrolyzing the reactor water by applying three types of different voltage-time waveform signals to the electrolytic cell; a process for determining the limiting current or peak current values, according to the kind of voltammetry employed, from the electrolysis current resulting from said electrolysis process and the voltage required to produce the electrolysis current; and a process for computing the concentrations of the $H_2$, $O_2$, and $H_2O_2$ in reactor water, based on the limiting current or peak current values thus determined.

2. The quantitative analysis for analysis of reactor water in a nuclear reactor method of claim 1, wherein the reactor water is brought into contact with the three electrodes in the electrolytic cell through a hydrophobic gas-permeable membrane.

3. The quantitative analysis method for analysis of reactor water in a nuclear reactor of claim 1, wherein the three electrodes in the electrolytic cell is brought into contact with the reactor water in the reactor by installing them in an in-reactor instrumentation column in the nuclear reactor.

4. A nuclear reactor water quality control system in which comprises a means of performing quantitative analysis, based on electrolysis, on the reactor water from the primary water-based cooling system of a nuclear reactor, and a means of controlling the water quality of reactor water, based on the results obtained from said quantitative analysis means, wherein said water quality control system comprises the following components: an electrode housing unit in an electrolytic cell, which is installed in at least one location in the said primary water-based cooling system so that the cell will come into contact with reactor water; a signal discharge unit which applies voltage-time wave signals having specified parameters to a working electrode in the said electrolytic cell as a reference electrode standard voltage; a signal input unit which inputs to the signal discharge unit voltage-time waveform signals having parameters which are determined by the type of voltammetry utilized, for each chemical species occurring in the primary water-based cooling system, and by changing the parameter for each chemical species involved; a storage unit which stores in memory the results of the voltammetry performed according to the signals supplied by the signal discharge unit, as a relationship between the electrolysis current and the voltage required to produce the electrolysis current; a current value determination unit which processes the data stored in the storage unit and which determines the limiting current or peak current, according to the type of voltammetry employed; a concentration computation unit which calculates the concentrations of the desired chemical species in the reactor water, based on the limiting current or peak current values thus determined; and a reactor water control means which regulates the water quality of the reactor water, based on the information produced by the concentration computation unit.

5. The nuclear reactor water quality control system of claim 4, wherein the voltage-time waveform signals which are input to the signal discharge unit comprises pulse mode waveform signals.

6. The nuclear reactor water quality control system of claim 4, wherein the chemical species computed by the concentration computation unit comprise at least one among $H_2$, $O_2$, and $H_2O_2$.

7. The nuclear reactor water quality control system of claim 4, wherein the electrolytic cell electrode housing unit is installed in the reactor core in the nuclear reactor.

8. The nuclear reactor water quality control system of claim 4, wherein the electrolytic cell electrode housing unit is installed in an electrolytic cell electrode housing unit is installed in an in-reactor instrumentaion column in the nuclear reactor.

9. The nuclear reactor water quality control system of claim 4, wherein the electrolytic cell electrode housing unit is installed on the reactor core outlet side of the primary water-based cooling system.

10. The nuclear reactor water quality control system of claim 4, wherein the electrolytic cell electrode housing unit is installed in the water vapor separator unit in the reactor.

11. The nuclear reactor water quality control system of claim 6, wherein the reactor water control means comprise a means of regulating the amount of $H_2$ gas that is injected into the primary water-based cooling system.

12. The nuclear reactor water quality control system of claim 6, wherein the reactor water control means comprise a means of regulating the amount of $N_2H_4$ that is injected into the water vapor generator in the reactor.

13. The nuclear reactor water quality control system of claim 12, wherein the quantity of $N_2H_4$ that is injected into the vapor generator is based on the quantitative analysis of dissolved $O_2$ gas in the primary water-based cooling system, computed by the concentration computation unit.

14. The nuclear reactor water quality control system of claim 4, wherein said system comprises a comparison unit which converts concentration values produced by the concentration computation unit to conductivity values and compares them with standard values, and reactor water control means that regulates the water quality in the reactor water by maintaining said converted values below standard values.

15. The nuclear reactor water quality control system of claim 4, wherein said system comprises a function generator between the signal discharge unit and the signal input unit, and the waveform signals produced by the signal input unit are entered in the signal discharge unit through the function generator.

16. A nuclear reactor water quality control system which comprises a means of performing quantitative analysis, based on electrolysis, on the reactor water from the primary water-based cooling system of the nuclear reactor, and a means of controlling the water quality of reactor water, based on the results obtained from the above quantitative analysis means, wherein the said water quality control system comprises the following components: an electrode housing unit in an electrolytic cell, which is installed in at least one location in the said primary water-based cooling system so that the cell will come into contact with reactor water; a signal discharge unit which applies voltage-time wave signals having specified parameters to a working electrode in said electrolytic cell as a reference electrode standard voltage; a signal input unit which inputs to the signal discharge unit voltage-time waveform signals having parameters which are determined by the kind of voltammetry utilized, for each chemical species occurring in the primary water-based cooling system, and by changing the parameter for each chemical species involved; a storage unit which stores in memory the results of the voltammetry performed according to the signals supplied by the signal discharge unit, as a relationship between the electrolysis current and the voltage required to produce the electrolysis current; a current value determination unit which processes the data stored in the storage unit and which determines the limiting current or peak current, according to the kind of voltammetry employed; a concentration computation unit which calculates the concentrations of the desired chemical species int he reactor water, based on the limiting current or peak current values thus determined; a comparison unit which compares the results of the said concentration computation unit with standard values; and a reactor water control means which regulates the water quality of the reactor water, based on the information produced by the comparison unit.

17. The nuclear reactor water quality control system of claim 16, wherein the provision of a comparison unit which compares with standard values the quality of at least one dissolved gas from among $H_2$, $O_2$, and $H_2O_2$ in the primary cooling water; and a means of regulating the quantity of at least one of the gas $H_2$, $O_2$, and $H_2O_2$ in the primary cooling water; and a means of regulating the quantity of at least one of the gases $H_2$, $O_2$, $H_2O_2$, that is injected into the reactor water, based on the information produced by the comparison unit.

18. The nuclear reactor water quality control system of claim 16, wherein the provided concentration computation unit generates equations in which the concentrations of the substances measured, and present in the reactor water, are treated as unknown variables, based on the limiting current or peak current values determined by the current determination unit; and calculates the concentrations of the substances by solving the set of equations.

19. The nuclear reactor water quality control system of claim 16, wherein said system comprises a means of measuring at least one of the following: reactor water conductivity, pH, or electric potential, at sampling points in the primary water-based cooling system; a comparison unit which compares the results of measurements with standard values; and the reactor water control means that regulates the water quality in the reactor water, based on the information produced by the said comparison unit and the said concentration comparison unit.

20. The nuclear reactor water quality control system of claim 16, wherein said system comprises a monitoring system which monitors the proper operation of the signal input unit, signal discharge unit, concentration computation unit, and comparison unit.

21. The nuclear reactor water quality control system of claim 20, wherein said system comprises a means of generating an alarm in the event that a malfunction is detected by the monitoring system.

22. A nuclear reactor preventive safety assurance system which comprises a means of performing quantitative analysis of reactor water in the primary water-based cooling system by electrolysis, and a means of generating an alarm when the results obtained by the quantitative analysis means exceeds a standard value; wherein said nuclear reactor preventive safety assurance system comprises the following components: an electrode housing unit in an electrolytic cell, which is installed in at least one location in the said primary water-based cooling system so that the cell comes into contact with reactor water; a signal discharge unit which applies voltage-time wave signals having specified parameters to a working electrode in the said electrolytic cell as a reference electrode standard voltage; a signal input unit which inputs to the signal discharge unit voltage-time waveform signals having parameters which are determined by the kind of voltammetry utilized, for each chemical species occurring in the primary water-based cooling system, and by changing the parameter for each chemical species involved; a storage unit which stores in memory the results of the voltammetry performed according to the signals supplied by the signal discharge unit, as a relationship between electrolysis current and the voltage required to produce the electrolysis current; a current value determination unit which processes the data stored in the storage unit and which determines the limiting current or peak current, according to the type of voltammetry employed; a concentration computation unit which calculates the concentrations of the desired chemical species in the reactor water, based on the limiting current or peak current values thus determined; a comparison unit which compares the results produced by the concentration computation unit with standard values; and an alarm generation means which generated an alarm when the results from the concentration computation unit exceeds a standard value.

23. The nuclear reactor preventive safety assurance system of claim 22, wherein said system comprises a means of measuring the concentrations of $SO_4^{2-}$, $SO_3-$, $Cl-$, and $Na^+$ ions, which are breakdown products of the nuclear reactor cleaning chemical resins in the primary water-based cooling system; and a means of generating an alarm when any one of the ionic concentrations exceeds a standard value.

24. A nuclear reactor water accident prevention system which comprises a means of performing quantitative analysis of reactor water in the primary water-based cooling system by electrolysis, and a means of predicting a reactor water accident, based on the results produced by the quantitative analysis means, wherein the said nuclear reactor water accident prevention system comprises following components and means: an electrode housing unit in an electrolytic cell, which is installed in at least on location in the said primary water-based cooling system so that the electrodes will come into contact with the reactor water a signal discharge unit which applies voltage-time wave signals having specified parameters to a working electrode in said electrolytic cell as a reference electrode standard voltage; a signal input unit which inputs to the signal discharge unit voltage-time waveform signals having parameters which are determined by the kind of voltammetry utilized, for each chemical species occurring in the primary water-based cooling system, and by changing the parameter for each chemical species involved; a storage unit which stores in memory the results of the voltammetry performed according to the signals supplied by the signal discharge unit, as a relationship between the electrolysis current and the voltage required to produce the electrolysis current; a current value determination unit which processes the data stored in the storage unit and which determines the limiting current or peak current, according to the kind of voltammetry employed; a concentration computation unit which calculates the concentrations in reactor water of the desired chemical species, based on the limiting current or peak current values thus determined; a comparison unit which compares the results produced by the concentration computation unit with standard values; and the said nuclear reactor water accident prevention system capable of predicting potential accidents in the primary water-based cooling system, based on the information produced by the comparison unit.

25. A nuclear reactor water quality control system which comprises a means of performing quantitative analysis by electrolysis of reactor water, such as the water found in boilers in a boiling water nuclear reactor, pressurized water nuclear reactor, or thermal power generating plant; and a means of regulating the quality of the reactor water, based on the results produced by the quantitative analysis means, wherein the said nuclear reactor water quality control system comprises the following components and means: an electrode housing unit in an electrolytic cell, which is installed in at least one location in the said primary water-based cooling system so that the electrodes will come into contact with the reactor water; a signal discharge unit which applies voltage-time wave signals having specified parameters to a working electrode in said electrolytic cell as a reference electrode standard voltage; a signal input unit which inputs to the signal discharge unit voltage-time waveform signals having parameters which are determined by the kind of voltammetry utilized, for each chemical species occurring in the primary water-based cooling system, and by changing the parameter for each chemical species involved; a storage unit which stores in memory the results of the voltammetry performed according to the signals supplied by the signal discharge unit, as a relationship between the electrolysis current and the voltage required to produce the electrolysis current; a current value determination unit which processes the data stored in the storage unit and which determines the lifting current or peak current, according to the kind of voltammetry employed; a concentration computation unit which calculates the concentrations of the desired chemical species in the reactor water, based on the limiting current or peak current values thus determined; and the reactor water control means which regulates the reactor water quality, based on the information produced by the concentration computation unit.

* * * * *